United States Patent [19]
Webster, Jr.

[11] Patent Number: 5,569,220
[45] Date of Patent: Oct. 29, 1996

[54] CARDIOVASCULAR CATHETER HAVING HIGH TORSIONAL STIFFNESS

[75] Inventor: Wilton W. Webster, Jr., Alta Dena, Calif.

[73] Assignee: Cordis Webster, Inc., Baldwin Park, Calif.

[21] Appl. No.: 367,690

[22] Filed: Dec. 30, 1994

Related U.S. Application Data

[63] Continuation of Ser. No. 60,494, May 11, 1993, abandoned, which is a continuation of Ser. No. 645,230, Jan. 24, 1991, abandoned.

[51] Int. Cl.⁶ ................................. A61M 25/00
[52] U.S. Cl. ................. 604/282; 604/114; 138/125; 128/639
[58] Field of Search ............... 604/280–282, 604/264, 114; 138/123–127, 132–134, 130, 144, 174, 109; 128/642, 633, 634, 639

[56] References Cited

U.S. PATENT DOCUMENTS

| | | | |
|---|---|---|---|
| 2,472,484 | 6/1949 | Krippendorf | 604/282 |
| 3,498,286 | 3/1970 | Polanyi et al. | 128/634 |
| 3,995,623 | 12/1976 | Blake | 128/642 |
| 4,213,462 | 7/1980 | Sato | 128/634 |
| 4,444,185 | 4/1984 | Shugar | 128/634 |
| 4,559,951 | 12/1985 | Dahl et al. | 128/642 |
| 4,585,035 | 4/1986 | Piccoli | 138/127 |
| 4,658,836 | 4/1987 | Turner | 128/642 |
| 4,817,613 | 4/1989 | Garaczewski et al. | 138/127 |
| 4,981,478 | 1/1991 | Evard et al. | 604/282 |
| 5,057,092 | 10/1991 | Webster, Jr. | 604/282 |

Primary Examiner—Randall L. Green
Assistant Examiner—Ronald K. Stright, Jr.
Attorney, Agent, or Firm—Christie, Parker & Hale, LLP

[57] ABSTRACT

A cardiovascular catheter comprises an elongated catheter body having a flexible plastic wall reinforced with at least two concentrically spaced-apart braided stainless steel meshes. The catheter exhibits high resistance to buckling and torsional stiffness to allow precise rotational control of the catheter tip.

18 Claims, 2 Drawing Sheets

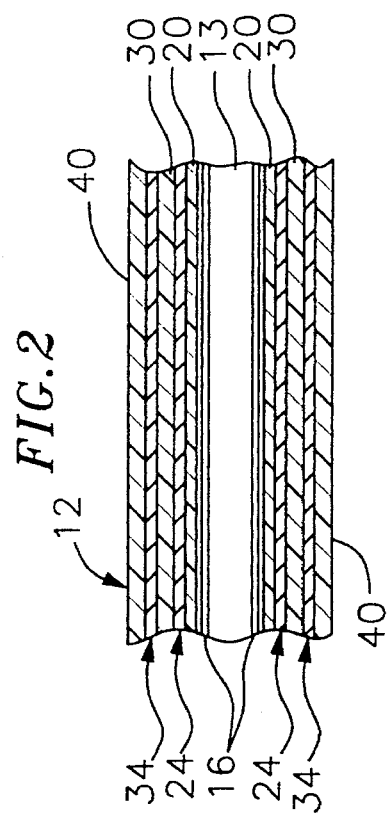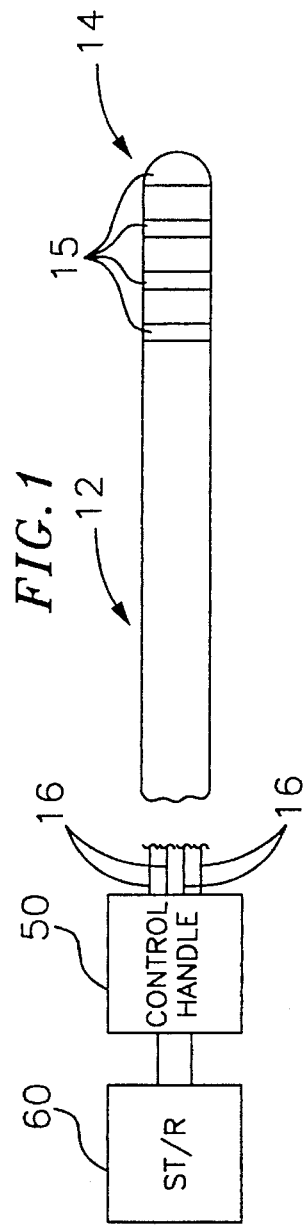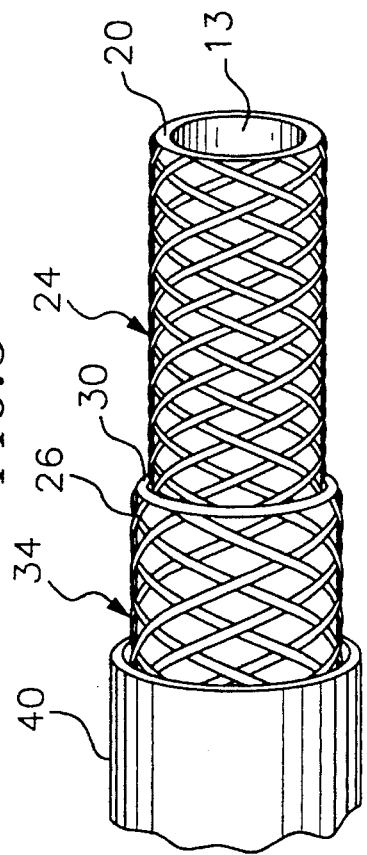

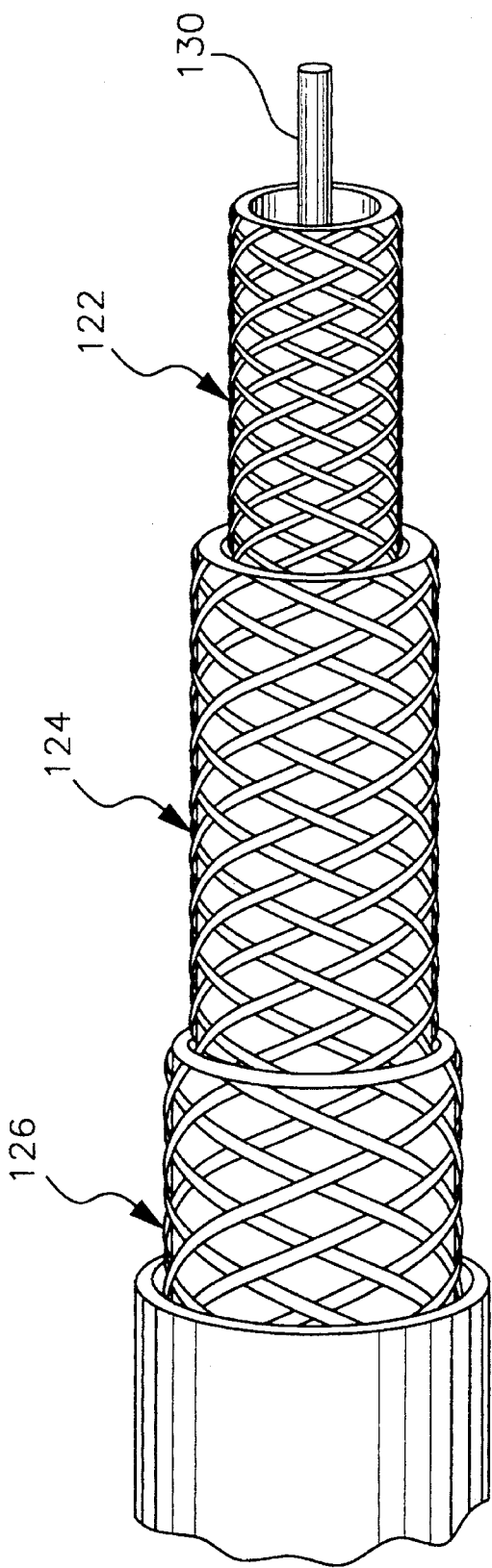
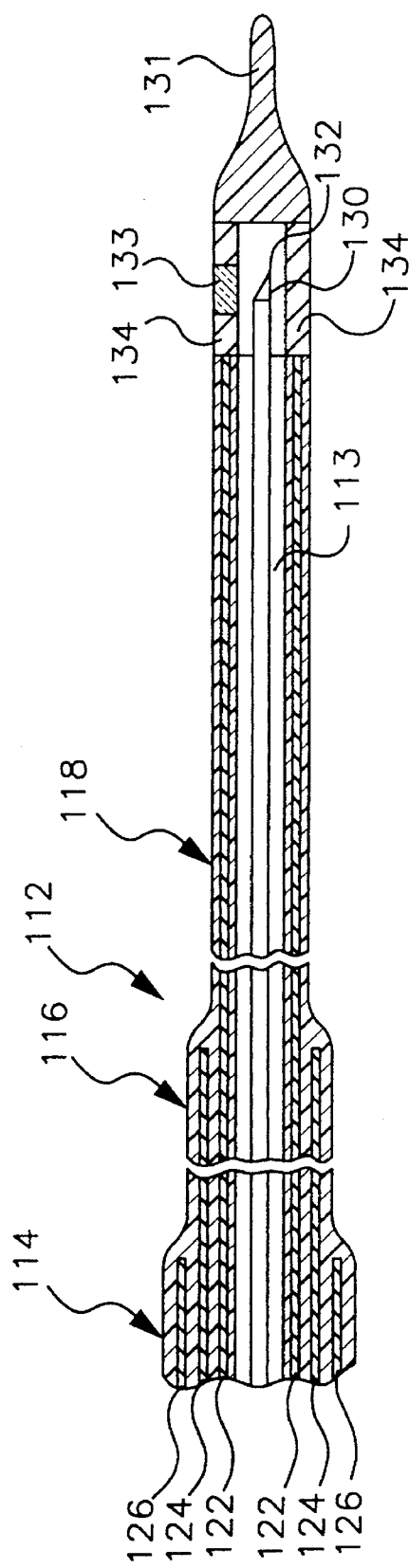

CARDIOVASCULAR CATHETER HAVING HIGH TORSIONAL STIFFNESS

CROSS-REFERENCE TO RELATED APPLICATIONS

This is a continuation of application Ser. No. 08/060,494, filed May 11, 1993, now abandoned which is a continuation of Ser. No. 07/645,230, filed Jan. 24, 1991 now abandoned.

FIELD OF THE INVENTION

The present invention relates to catheters, and more particularly to a cardiovascular catheter having an elongated catheter body reinforced with multiple spaced-apart layers of stainless steel braided meshes to provide high torsional stiffness.

BACKGROUND OF THE INVENTION

Some catheters require relatively accurate positioning and orientation of their tips, such as cardiovascular electrode catheters and coronary angioplasty and other balloon catheters.

Cardiovascular electrode catheters are used to electrically stimulate and/or monitor or map the heart and to ablate tissue, e.g., to remove an unwanted electrical pathway. Accordingly, precise control of the catheter tip is critical. Many such catheters have steerable tips which can be deflected by operation of a control handle. Manipulation of the catheter tip generally involves deflection of the steerable tip and/or rotation of the catheter by the operating physician.

Cardiovascular electrode catheters are typically inserted into the femoral vein or artery and advanced into the heart. The pathway involves vascular curves which must be navigated to arrive at the desired heart location and the catheters must be sufficiently flexible to bend around these curves. Such bending, however, tends to result in a loss of control of the catheter tip. This is because the portion of the catheter which bends around a curve tends to resist rotation. Resistance to rotation continues until a threshold level of torsional energy is reached. At that point, the curved portion of the catheter tends to flop over with a resultant loss of tip control.

In other catheters, tip control and orientation may be even more critical. For example, in a laser catheter comprising an optical fiber for delivering laser radiation to oblate a stenotic lesion, precise tip positioning and orientation is necessary, particularly when a prism, mirror or the like is used to deliver the laser radiation off-axis and onto the lesion.

In view of the above, there is a need for a catheter having a resilient, flexible body, yet sufficient torsional stiffness to allow precise tip control.

SUMMARY OF THE INVENTION

The present invention provides a catheter which exhibits high torsional stiffness to provide precise tip control while maintaining high flexibility and resiliency. Catheters of the present invention comprise an elongated tubular body reinforced with two or more braided meshes. The braised meshes are preferably made of stainless steel wire and are preferably concentrically spaced apart.

In a preferred embodiment of the invention, the catheter is an electrode catheter having one or more electrodes at its distal end connected by wires to a source of electrical energy at the proximal end of the catheter. The catheter body is reinforced with a pair of concentric braided meshes.

In another preferred embodiment, the catheter contains an optical fiber for delivering laser irradiation to stenotic lesions in arteries. The catheter comprises an elongated body reinforced with two or more concentric braided meshes.

In a another embodiment of the invention, there is provided a cardiovascular catheter which may be an electrode catheter, a laser catheter, or the like. The catheter comprises an elongated body having a first section which extends most of the length of the catheter which is reinforced with three concentric braided meshes. A second section comprises two concentric braided meshes. The tip comprises a third section having a single braided mesh. In use, the first section extends up to the arch of the aorta, the second section extends over the aortic arch, and the third section extends into the coronary arteries. Such catheter construction provides high torsional stiffness up to the aortic arch, a combination of high torsional stiffness with increased flexibility over the aortic arch, and further increased flexibility at the tip which extends into the coronary arteries.

BRIEF DESCRIPTION OF THE DRAWINGS

These and other features and advantages of the present invention will be better understood by reference to the following detailed description when considered in conjunction with the accompanying drawings wherein:

FIG. 1 is a schematic view of a cardiovascular electrode catheter constructed in accordance with the present invention also showing a control handle and a stimulator/recorder device;

FIG. 2 is a fragmentary, side cross-sectional view of the catheter of FIG. 1;

FIG. 3 is a cut-away perspective view of the catheter body of the catheter according to FIG. 2;

FIG. 4 is a side cross-sectional view of a catheter constructed in accordance with the present invention comprising an optical fiber extending through its lumen; and FIG. 5 is a cut-away perspective view of the catheter body of the catheter according to FIG. 4.

DETAILED DESCRIPTION

With reference to FIGS. 1–3, there is shown a preferred cardiovascular catheter constructed in accordance with the present invention. The electrode catheter comprises an elongated tubular body 12 having a central lumen 13 and a tip 14 comprising a plurality of spaced-apart electrodes 15.

The tubular catheter body 12 comprises an inner wall 20, a first braided reinforcing mesh 24 surrounding the inner wall 20, an intermediate wall or layer 30 surrounding the first braided reinforcing mesh 24, a second braided reinforcing mesh 34 around the intermediate layer 30, and an outer wall or layer 40. The inner, intermediate and outer walls 20, 30 and 40 are made of a flexible, nontoxic plastic material such as polyurethane, PVC or the like as is well known in the art.

Each of the first and second braided reinforcing meshes 24 and 34 comprise interwoven helical braid members 26. Each reinforcing mesh typically comprises twelve, sixteen or twenty-four interwoven helical members, half extending in one direction and the other half extending in the counter direction. The tightness or braid angle of the helical members 26, i.e., the angle, to a line parallel with the axis of the catheter and intersecting the helical members is not critical but is preferably about 45°. An angle less than about 45° is less preferred because as the braid angle becomes smaller, there is a greater tendency for the catheter to buckle when bent. Further, such catheters tend not to transmit torque around corners as well as catheters having higher braid angles. Braid angles greater than about 45° are not preferred because they do not appear to offer any advantage and are less economical.

The helical members 26 are preferably made of a material having a high modulus of elasticity. Preferred helical members are made of stainless steel wire, although, depending on the application, materials such as Kevlar thread, marketed by DuPont, and Specter Fiber, a modified polyethylene material marketed by Allied Signal, may be used.

Copper wires 16 are electrically connected to the electrodes and extend through the catheter body lumen and then to a handle or connector (represented by box 50). If desired, the electrode lead wires may be incorporated in a braid layer or embedded in the catheter wall. The handle or connector 50 can be plugged, directly or through an extension cord, into an electrical stimulator and/or recorder or the like, represented by box 60 (ST/R). If desired, the tip may be made steerable, as described in U.S. Pat. No. 4,960,134 to Webster, Jr., which is incorporated herein by reference.

The tip 14 may be closed at its distal end or may comprise a central lumen communicating with the central lumen of the catheter body an open distal end. An open ended lumen 13 allows substances to be passed through the catheter, e.g., for taking blood samples or passing optical fibers.

If a highly flexible tip is desired, the reinforcing meshes 24 and 34 of the catheter body will not extend into the tip. It is understood, however, that one or both of the reinforcing meshes could extend into the tip if desired.

The two layers of reinforcing braided mesh may be adjacent and in contact with each other, but are preferably concentrically spaced-apart by a layer of plastic. Such a construction provides a flexible yet resilient catheter body having superior buckling or kink resistance and provide better rotational control of the catheter. Increasing the space between the mesh layers increases the resistance to kinking or buckling when the catheter is curved around a vascular bend. The improved rotational control minimizes the tendency of the catheter tip to flop over when the catheter is rotated. This allows the tip to be very accurately oriented.

The catheter may be made by a conventional braiding process. In such a process, the braid members of the first reinforcing mesh are interwoven, under tension, around the inner plastic wall. The intermediate layer is then applied by dipping, spraying, extrusion or any other suitable process. The braid members of the second mesh are then interwoven, under tension, around the intermediate layer. The outer layer is then applied around the second mesh, again by dipping, spraying, extrusion or any other suitable process.

The inner and outer diameters of the catheter body 12, as well as the diameters of the helical members, will depend on the particular application. For example, in a cardiovascular electrode catheters having a French size of 7, the catheter body has an outer diameter of about 0.091 inch. In such a catheter, the inner diameter will generally be from about 0.04 to about 0.060 inch. This provides a lumen sufficiently large to accommodate the copper electrode leads 15 which extend from the electrodes to the stimulator or recorder 60 plus a safety wire which is typically attached to the tip electrode and/or a puller wire if the catheter has a steerable tip.

Like the inner and outer diameters of the catheter body, the diameter of the stainless steel wire which forms the first and second reinforcing meshes depends on the application.

A stainless steel wire diameter of approximately 0.0026 inch is presently preferred for most cardiovascular electrode catheters. A spacing of from about 0.002 to about 0.010 inch and preferably about 0.005 inch between the braided mesh layers is presently preferred.

It should be noted that although the above embodiment has been shown with two concentrically spaced-apart braided layers, additional braided layers may be used.

The invention is also particularly applicable to the construction of a laser catheter for use in ablating atherosclerotic plaque deposits. Accordingly, in another embodiment of the invention, there is provided a coronary laser catheter, as shown in FIGS. 4 and 5, which comprises an elongated catheter body 112 having a hollow lumen 113. The body 112 is again constructed out of a suitable biologically non-reactive material, e.g., polyurethane.

The catheter body comprises three sections: a first or proximal section 114, a second or middle section 116, and a third or tip section 118. During use, the proximal section 114 extends from the insertion point along the aorta up to the aortic arch. The second section 116 extends over the aortic arch, a distance of about six inches. The tip 118, which extends into the coronary artery, is generally about 6 inches long.

In the proximal section 114, the catheter body comprises first, second and third concentrically spaced-apart layers 122, 124 and 126 of reinforcing braided stainless steel mesh. In the second section 116, there are only first and second layers 122 and 124, and the tip 118 comprises the first layer 122. This catheter construction provides very high torsional stiffness with reduced flexibility along most of the length of the catheter, increased flexibility while maintaining high torsional stiffness over the aortic arch, and high flexibility with reduced torsional stiffness at the tip.

In the embodiment shown, the laser catheter body has a central lumen 113. At the distal end of the catheter body, there is provided a nose piece 131 made of soft, flexible material. One or more optical fibers 130 extend through the lumen 113 to a position adjacent a window 133, made of quartz or the like which is mounted in a rigid housing 134 adjacent the nose piece 131. The optical fiber has a mirror or prism 132 at its distal end. The optical fibers 130 are used to deliver laser radiation off axis through window 133 for ablating plaque deposits. It is apparent that rotational control of the tip of the laser catheter is critical for the effectiveness of the catheter. The present invention provides such rotational control. Other examples of the use of optical fibers to deliver laser radiation to a plaque deposit are described in U.S. Pat. Nos. 4,576,177 and 4,641,650 which are incorporated herein by reference.

The preceding description has presented with reference to the presently preferred embodiments of the invention shown in the drawings. Workers skilled in the art and technology to which this invention pertains will appreciate that alterations and changes in the described structures can be practiced without meaningfully departing from the principle, spirit and scope of this invention.

For example, it is apparent that a laser catheter may be constructed according to the invention wherein the proximal section of the catheter body comprises two layers of reinforcing braided mesh, the middle section comprises a single layer of braided mesh, and the tip is unreinforced. In yet another embodiment, the proximal and middle sections may comprise two layers of reinforcing mesh, and the tip may comprise a single layer or none at all.

It is also understood that the present invention is applicable to catheters other than electrode and laser catheters.

For example, the present invention may be used to enhance the tip control of conventional balloon angioplasty catheters and hence, to enhance the positioning of the balloons in coronary arteries.

Accordingly, the foregoing description should not be read as pertaining only to the precise structures described and shown in the accompanying drawings, but rather should be read consistent with and as support to the following claims which are to have their fullest and fair scope.

What is claimed is:

1. A catheter adapted for insertion into a blood vessel of a human patient, said catheter exhibiting high torsional stiffness and comprising:

an elongated catheter tubular body having a proximal end and a distal end, said body comprising a wall, said wall comprising inner, intermediate and outer layers of flexible non-toxic plastic material, a first tubular braided reinforcing mesh between the inner and intermediate layers and a second tubular braided reinforcing mesh between the intermediate and outer layers so that the first and second tubular braided reinforcing meshes are disposed in the wall in concentric relation, wherein the first and second meshes comprise metal and are sandwiched between the inner and outer plastic layers and are spaced apart by the intermediate plastic layer without touching each other for increasing stiffness of the catheter body.

2. A catheter as claimed in claim 1 wherein the braided reinforcing meshes are made of stainless steel.

3. A catheter as claimed in claim 1 wherein the braided reinforcing meshes are concentrically spaced apart a distance of from about 0.002 inch to about 0.010 inch.

4. A catheter as claimed in claim 1 wherein the braided reinforcing meshes are concentrically spaced apart a distance of about 0.005 inch.

5. The catheter of claim 1 wherein the intermediate plastic layer consists essentially of plastic.

6. A steerable cardiovascular electrode catheter comprising an elongated catheter body having a proximal end and a distal end, said body comprising a solid tubular plastic wall, said wall comprising inner and outer layers, and at least one solid tubular plastic intermediate layer, and at least two tubular concentric braided meshes extending throughout the length of the body and a tip extending from the distal end of the body, said tip carrying a plurality of electrodes, wherein the meshes comprise metal and are sandwiched between the inner and outer plastic layers and are spaced apart without touching each other by the at least one intermediate layer for increasing stiffness of the catheter body.

7. A catheter as claimed in claim 6 wherein the concentric braided meshes are spaced apart a distance of from about 0.002 inch to about 0.010 inch.

8. A catheter as claimed in claim 6 wherein at least one braided mesh extends into the tip.

9. The catheter of claim 6 wherein the metal is stainless steel.

10. The catheter of claim 6 wherein the catheter wall between the two meshes consists essentially of plastic.

11. A catheter comprising an elongated tubular catheter body having a proximal section, a middle section, and a tip section wherein:

the proximal section comprises a wall comprising inner and outer layers of flexible, non-toxic plastic material reinforced with at least two layers of tubular braided mesh therebetween, said layers of braided mesh being concentrically spaced apart by at least a middle layer of flexible, non-toxic plastic material; and the middle section comprises a wall comprising inner and outer layers of flexible, non-toxic plastic material reinforced with at least one layer of tubular braided mesh therebetween, wherein the layers of mesh comprise metal and are sandwiched between the inner and outer plastic layers and are spaced apart by the middle layers of plastic material without touching each other for increasing stiffness of the proximal section.

12. A catheter as claimed in claim 11 wherein the catheter comprises a central lumen which is open at the distal end of the catheter, and wherein the catheter comprises at least one optical fiber extending through the catheter lumen.

13. A catheter as claimed in claim 12 wherein the optical fiber comprises a prism at its distal tip.

14. A catheter as claimed in claim 12 wherein the optical fiber comprises a mirror at its distal tip.

15. A catheter as claimed in claim 11 wherein the middle section is about 6 inches in length.

16. A catheter as claimed in claim 11 wherein the tip section is about 6 inches in length.

17. The catheter of claim 11 wherein the metal is stainless steel.

18. The catheter of claim 11 wherein the middle layer consists essentially of plastic.

* * * * *